United States Patent
Kurtz et al.

Patent Number: 5,724,401
Date of Patent: Mar. 3, 1998

[54] LARGE ANGLE SOLID STATE POSITION SENSITIVE X-RAY DETECTOR SYSTEM

[75] Inventors: David S. Kurtz; Clay O. Ruud, both of State College, Pa.

[73] Assignees: The Penn State Research Foundation, University Park, Pa.; Advanced Technology Materials, Inc., Danbury, Conn.

[21] Appl. No.: 590,956

[22] Filed: Jan. 24, 1996

[51] Int. Cl.⁶ .................................................. G01N 23/20
[52] U.S. Cl. ........................ 378/171; 378/71; 378/98.8
[58] Field of Search ........................ 378/70, 71, 72, 378/73, 98.8

[56] References Cited

U.S. PATENT DOCUMENTS

| | | |
|---|---|---|
| 3,483,377 | 12/1969 | Borkowski . |
| 4,026,693 | 5/1977 | Sato . |
| 4,076,981 | 2/1978 | Sparks . |
| 4,489,425 | 12/1984 | Borgonovi . |
| 4,530,565 | 7/1985 | Markle . |
| 4,549,204 | 10/1985 | Bertero . |
| 4,634,490 | 1/1987 | Tatsumi . |
| 4,649,556 | 3/1987 | Rinik . |
| 4,715,053 | 12/1987 | Comstock . |
| 4,800,580 | 1/1989 | Houtman . |
| 4,824,194 | 4/1989 | Karasawa . |
| 4,910,758 | 3/1990 | Herrick . |
| 4,932,747 | 6/1990 | Russell . |
| 5,003,570 | 3/1991 | Whiting . |
| 5,073,918 | 12/1991 | Kamon . |
| 5,125,016 | 6/1992 | Korhonen et al. .................. 378/72 |
| 5,136,674 | 8/1992 | Kakiuchi . |
| 5,155,751 | 10/1992 | Chohata . |
| 5,216,738 | 6/1993 | Feder . |
| 5,268,978 | 12/1993 | Po . |
| 5,373,544 | 12/1994 | Goebel . |
| 5,414,747 | 5/1995 | Ruud et al. ......................... 378/72 |
| 5,418,828 | 5/1995 | Carpenter . |

*Primary Examiner*—Don Wong
*Attorney, Agent, or Firm*—Thomas J. Greer, Jr.

[57] ABSTRACT

A method and apparatus for x-ray measurement of certain properties of a solid material. In distinction to known methods and apparatus, this invention employs a specific fiber-optic bundle configuration, termed a reorganizer, itself known for other uses, for coherently transmitting visible light originating from the scintillation of diffracted x-radiation from the solid material gathered along a substantially one dimensional linear arc, to a two-dimensional photo-sensor array. The two-dimensional photodetector array, with its many closely packed light sensitive pixels, is employed to process the information contained in the diffracted radiation and present the information in the form of a conventional x-ray diffraction spectrum. By this arrangement, the angular range of the combined detector faces may be increased without loss of angular resolution. Further, the prohibitively expensive coupling together of a large number of individual linear diode photodetectors, which would be required to process signals generated by the diffracted radiation, is avoided.

10 Claims, 4 Drawing Sheets

LARGE ANGLE SOLID STATE POSITION SENSITIVE X-RAY DETECTOR SYSTEM

This invention was made with Government support under Contract No. DE-FG05-92ER81327 awarded by the U.S. Department of Energy. The Government has certain rights in this invention.

FIELD OF THE INVENTION

The present invention relates to a solid state, large angle linear x-ray detector (with no moving parts or gaseous components), and to the applications of such a system for x-ray diffraction.

BACKGROUND OF THE INVENTION

The technique of x-ray diffraction involves the constructive interference of x-rays with regularly spaced atoms in a material. Whenever x-rays encounter a crystalline material they are scattered in all directions. However, in certain angular directions there is a phase matching of the scattered x-ray waveform. This results in a high x-ray intensity relative to the background scattered intensity at certain angular directions. When one observes the scattered x-rays over a large angular range, high intensity, constructive interference regions are referred to as diffraction peaks, and are related to the inter-atomic planar spacing of specific crystallographic planes. The Bragg equation is used to equate the inter-atomic planar spacing to the x-ray wavelength and the angle at which the peaks occur (referred to as the Bragg angle). The relation is written as:

$$n\lambda = 2d \sin\theta$$

where, n is typically unity for a polycrystalline material $\lambda$ is the wavelength of the diffracting x-rays d is the interplanar spacing of a particular crystallographic plane $\theta$ is the Bragg angle The breadth, intensity, and position of the diffraction peaks which make up the x-ray diffraction spectrum of a material provide a powerful tool for determining chemical phase composition and microstructure (degree of crystallinity, preferred orientation, grain size, film thickness, and elastic strain). However, the technique is typically limited to time consuming ex-situ analysis of small samples.

Modern commercial scanning x-ray diffractometers commonly employ a Bragg-Brentano focusing geometry, and employ rotation of a sample at a given angular speed of X° per minute, and separate rotation of a point detector at 2X° per minute to cover a large angular range in one dimension. A commonly used detector is a scintillation crystal connected to a photomultiplier tube. A precision goniometer is required to rotate both the sample and the detector at different angular speeds in order to capture the desired range of the x-ray diffraction spectrum. The goniometer is bulky and heavy and imposes limits on the size of the sample, making it ill suited for adaptation to real-time process monitoring and control. Since only a fractional angular increment is measured at one time, slow data acquisition times result when an angular range is to be interrogated, making observation of rapid material changes impossible.

Some improvement in the data acquisition speed has been achieved using linear position sensitive proportional detectors (PSPD's). They operate on the principle of x-rays interacting with an ionizing gas and creating a measurable current at discreet positions on a long anode wire (or blade). The position of x-rays on the anode are determined by a delay-line readout method. Both the anode and gas are contained within a sealed detector chamber. Gas proportional detectors are commonly used as both point detectors and one dimensional position sensitive detectors (both curved and straight), but have also recently been expanded to two dimensional operation (General area detector diffraction system, GADDS™ produced by Siemens, 6300 Enterprise Lane, Madison, Wis.). PSPD's have limited flux capacity, limited resolution, are quite bulky, require regular maintenance of the gas chamber and anode elements, and must be completely redesigned if different curvatures are desired.

A linear position sensitive proportional gas detector, with an active detector length of approximately 10 cm, has been applied to a traditional Bragg-Brentano scanning diffractometer by Goebel to reduce the required data acquisition time, as described in U.S. Pat. No. 4,301,364. Goebel also applied it to a Guinier diffraction system as described in published work (Advances in X-ray Analysis, 25, 315–324, [1982]). In U.S. Pat. No. 4,076,981 a curved position sensitive proportional detector is applied to an x-ray camera in both fixed and rotating configurations.

Inel Inc. (Z. A. de Courtaboeuf, Avenue de Scandinavie, 91953 Les Ulis, Cedex, France) manufactures a large curved linear position sensitive proportional detector (model CPS120) coupled to a conventional x-ray source. A flat germanium crystal monochromator is incorporated between the source and the sample. The Inel system has an angular range of 120° 2$\theta$, an active curved detector length of 52 cm, and a designed detector circle radius of 25 cm. The quoted angular resolution of the Inel system is 0.03° 2$\theta$, which equates to linear spatial resolution of 130 µm. To improve resolution Inel produces a larger curved PSPD (model CPS 590) with a 50 cm detector circle radius, where the resolution is improved by 35% to 0.024° 2$\theta$. Normally doubling the radius would increase the resolution by ~100%, but the effect is partially negated by a lower efficiency of the delay line readout method.

In another related U.S. Pat. No. 4,800,580, issued to Houtman and Brouwer, a curved photo-diode, one dimensional (1-D) position sensitive x-ray detector is described. The invention employs multiple linear silicon diode arrays that act as a direct detector of the diffracted x-ray beam. A large number of these silicon diode arrays are proposed to be arranged in various focusing geometries to perform x-ray diffraction analysis. Unlike the current invention, U.S. Pat. No. 4,800,580 does not employ any type of fiber-optic array(s) between the diffracted x-ray signal and the silicon diode photo-sensing arrays. The multiple silicon diode arrays must be fabricated, and attached both geometrically and electronically in a precise fashion, to form the 1-D position sensitive detector. As with any silicon diode array directly exposed to typical diffraction x-ray sources, radiation damage will cause the diodes to continually degrade over time. This not only limits the life of the diode array, but necessitates that background readings be taken after every measurement, due to accumulating background noise.

Imaging two dimensional photo-sensor arrays such as CCD's (charge couple devices) have been used in real time two-dimensional x-ray imaging (Model SCX-TE/CCD-1242E x-ray imaging camera produced by Princeton Instruments, Trenton, N.J.; Nonius CCD camera made by Nonius Delft Instruments, Delft, Netherlands; and Texray™ CCD camera made by Molecular Structure Corporation, The Woodlands, Tex.). Typically, a two dimensional (2-D) fiber-optic bundle, which is often tapered, is mated to the CCD. A scintillation coating is applied to the exposed face of the fiber-optic bundle. X-rays impinging on the detector surface are first converted to visible light by the scintillation coating. Light is transported along the fiber-optic array and digitized by the CCD.

Two dimensional fiber-optic photo-sensor array x-ray detectors are primarily used to generate rapid 2-D Laue diffraction patterns for analysis of small crystalline samples (organic or inorganic, often with complex crystal structures). They are optimized for 2-D x-ray image detection. In this application single diffraction points are generated over a two-dimensional region. Particular groups of diffraction points are associated with curves that represent the Laue reflection of individual crystallographic planes. Often the sample is rotated in numerous directions to ensure illumination of many crystallographic planes. 2-D Laue diffraction patterns provide information on crystal structure, orientation, and degree of crystal perfection. These two dimensional detectors are not optimized for traditional powder x-ray diffraction techniques which cover large angular ranges in one dimension.

In addition to crystallography, two dimensional fiber-optic photo-sensor array x-ray detectors have been used for real time medical x-ray imaging over a limited area. A scintillation coating is placed on the face of the fiber-optic taper to convert the x-rays to visible light. The resulting output is a picture image (similar to a television image) of critical internal structure such as bones, tissue, organs, etc. It is obvious that a 2-D detector is desirable in this application. A 2-D tapered fiber-optic is commonly used to make the imaging area large enough to be useful (such as looking at a knee joint).

One-dimensional fiber-optic coupled position sensitive x-ray diffraction detectors are described in U.S. Pat. Nos. 5,148,458 and 4,686,631, both issued to Ruud. These detectors are part of an apparatus and method for determining residual stress in crystalline materials. They employ the same general technique as the area x-ray detectors to digitize the x-ray signal. X-rays are converted to visible light by a scintillation coating placed on the input ends of fiber-optic bundles. The light is transported by the fiber-optic bundle to a linear photo-sensor array where it is digitized. The Ruud detectors make use of linear diode arrays to which the fiber-optic bundles have been mated. They have a limited active detector length of only 2 to 3 cm, which is all that is required for x-ray diffraction based stress measurements. U.S. Pat. No. 4,489,425 issued to Borgonovi describes the use of a 2-D multi-pixel light detector array mated to a fiber-optic bundle for recording a 2-D diffraction cone, but also covers only a limited angular range specifically for the purpose of stress analysis.

SUMMARY OF THE INVENTION

The present invention relates to a new fiber-optic based x-ray detector referred to as a Large Angle Solid State Position Sensitive X-ray Detector (LASS-PSXRD), specifically designed for large angle rapid diffraction analysis in one dimension. The detector system is capable of simultaneously covering a large angular range in one dimension with high resolution, high flux capabilities, no moving parts, and no gaseous chambers. It makes use of a commercially available two-dimensional multi-pixel photo-sensor array (such as a CCD), and combines with it a fiber-optic array, referred to as a 'reorganizer'. The fiber- optic reorganizer effectively takes the large number of pixels that are available in a two-dimensional photo-sensor array and reorganizes them into a substantially linear array, the latter forming the x-ray detector face. This face can be easily curved and positioned to match the particular focusing arc or detector circle of the specific x-ray geometry selected. The detector face is coated with a scintillation material that converts the diffracted x-rays emanating from a sample bombarded with x-rays into a light signal, which is then transported along the fiber-optic bundles. The light signal impinges upon the 2-D multi-pixel light detecting array which in turn creates a large number of electrical signals. The individual pixels in the 2-D array are grouped or 'binned' into an appropriate array of 'composite-pixels', which will produce a conventional line scan diffraction pattern or variations thereof. The output signals from the 2-D array are transferred to a personal computer, digitized and stored as a full diffraction pattern. The present invention thus senses diffracted and/or scattered x-rays along an essentially 1-D arc, converts the x-rays to visible light visible, and reorganizes the visible onto a 2-D photo-sensor array, which in turn reconverts the 2-D light signal into a 1-D output signal.

Compared to 1-D position sensitive gas proportional detectors, the LASS-PSXRD system is all solid state, is capable of higher resolution at smaller focal distances, has higher flux limits and a greater dynamic range, is lower in maintenance (no gas chambers to maintain), more compact, and can be readily modified to different focusing geometries. The x-ray beam impinging on the detector need not be normal to the detector surface at all positions on the detector surface. A practical spatial resolution limit of the present invention is about 45 µm, factoring in all machine peak broadening effects, which is 2.8 times better than the 130 µm resolution limit of typical position sensitive proportional detectors, such as the Inel curved proportional counter. The resolution increase becomes more pronounced at larger focal distances since the fiber-optic detector does not suffer from efficiency loss of the time delay counting as the length of the linear proportional counter increases.

Compared to high speed scanning diffractometers, there are no moving parts in the LASS-PSXRD, and data acquisition times are up to 100 times faster. The LASS-PSXRD can be tailored for different diffraction geometries, angular ranges, and angular resolution by quickly repositioning the fiber-optic portion of the detector, while the 2-D multi-pixel photo-sensor array portion of the system remains constant. The more sensitive electronic components of the detector can be remotely isolated from the more durable fiber-optic detector head itself. All of these attributes enable the present LASS-PSXRD system to be easily optimized for many different specialty x-ray diffraction applications, especially for real time process monitoring and control in manufacturing environments.

The number of rectangular fiber-optic bundles of the reorganizer, the overall size of the multi-pixel array, and the individual pixel size can be varied depending on the desired angular range, angular resolution, and focal distance. Tapered fiber-optic bundles can provide added control over the angular range and resolution of the detector. The invention will work with any fiber-optic compatible 2-D photo-sensor array. The main advantage of using a CCD system over a diode array or CID (charge injection device) is the combination of low noise and large choice of pixel count and the pixel size available. Low noise, fiber-optic compatible CCD arrays of numerous sizes are commercially available. Not all applications will require a combination of large angular range with high resolution, thus smaller pixel count arrays would be applicable in certain situations.

There are several focusing geometries that are used in x-ray diffraction work. The present detector can be configured to work with all of them. Each geometry has different advantages and disadvantages.

Commercial scanning diffractometers commonly use para-focusing conditions (also referred to as Bragg-Brentano or θ/2θ focusing). In this geometry the sample is rotated at some angular speed ω and typically a point detector is rotated at twice the angular speed 2ω. The rotating apparatus is referred to as a goniometer. It maintains the incident beam angle on the sample surface, and the diffracted beam angle on the sample surface that the detector observes, at equal values. The bisector of incident and diffracted angle will always be perpendicular to the sample surface. The sample is located at the center of a detector circle of constant diameter. As the rotation process proceeds the diameter of the focusing circle (in contrast to the detector circle) actually changes. Linear position sensitive detectors with an angular range of ~10° (5 to 10 cm in length) have been used with this focusing geometry. Unlike point detectors, collimating slits and monochromators cannot be used between the sample and a position detector to improve resolution (they would reduce the position sensitive detector to a point detector, negating their intended function). At any one given position there is only one point on the detector that is truly in focus (the θ position). The other points on the detector are out of focus. Thus limiting the active length of the position sensitive detector limits the defocusing effect to acceptable values.

A variation on the para-focusing Bragg-Brentano geometry is to use a constant diameter detector circle employing a near parallel, microfocused x-ray beam. Using an appropriate collimating slit and/or monochromator, the size of the incident x-ray beam is reduced to a very small diameter (less than about 200 microns depending on the radius of the detector circle), and is made nearly parallel (non-divergent). With a parallel beam the resolution of a position sensitive detector is limited by the beam size, and not the sample-to-detector distance. Thus a curved linear position sensitive detector could be placed at different radii from the irradiated area and always be in focus, at all angular positions on the detector. It is advantageous to fix the position sensitive detector at a constant radius, as illustrated in FIG. 1. This geometry is presently used with the Inel (Cedex, France) model CPS 120 curved gas proportional detector.

There are several disadvantages of this technique. It reduces the x-ray flux significantly, requiring longer counting times. It also significantly reduces the number of grains irradiated by the incident beam. This will often result in poor counting statistics of certain diffraction planes. The effect can partially overcome by varying degrees of rotation of the sample in the beam to enable all possible diffraction planes to be observed.

Another focusing geometry used in x-ray diffraction is the Seemann-Bohlin, or Guinier focusing geometry. This geometry does require rotation of detector or sample, and can be employed in both transmission and reflection. It was originally designed for use with x-ray film. In this geometry the sample is not on the center of the detector circle but instead forms one of the points on the perimeter of the focusing circle. It is illustrated in FIG. 2. In contrast to the detecting circle, x-rays will intersect the focusing circle at varying incident angles.

The Seemann-Bohlin geometry has the advantage of enabling a much greater x-ray flux reaching the detector, and a much larger irradiated area on the sample surface, thus providing much improved counting statistics (over the micro-focused, near-parallel beam approach). It has the disadvantage in that it requires the position sensitive detector to be able to compensate for a variable angle of incidence of x-rays on the detector surface. Assuming a lower 2θ limit of 20° this incident angle could be as low as 15°. Linear gas proportional detectors exhibit significant signal smearing when a perpendicular angle is not maintained, and have not been successfully applied to the geometry shown in FIG. 2. The present invention includes a method which compensates for variable x-ray incidence angle on the detector, without the smearing effect that occurs in position sensitive gas proportional counters.

A third focusing geometry is the Debye-Scherrer geometry. It relies on the use of very small controlled sample size and shape, and a forward diffraction mechanism. A pinhole collimator creates a near parallel beam of small cross-sectional area. Debye-Scherrer utilizes a fixed geometry, but is not very applicable to routine analysis due to intricate sample preparation procedures. The present invention could be applied to the Debye-Scherrer geometry as well.

It is an object of the present invention to provide an all solid state, large angle, flexible geometry, high resolution, one dimensional position sensitive x-ray detector for x-ray diffraction applications. The x-ray diffraction applications include measurement of phase composition, crystallinity, preferred orientation, crystallite size, thickness, and elastic strain in both off-line (i.e., ex-situ) analysis, portable field analysis, and on-line (i.e., in-situ) analysis/monitoring and feed-back control.

It is another object of the invention to employ a fiber-optic reorganizer in conjunction with a 2-D multi-pixel photo-sensor array. The fiber-optic reorganizer utilizes the large number of pixels available in a 2-D photo-sensor array and converts them to a curved, essentially one dimensional x-ray detector array for high resolution diffraction analysis over a large angular range. The number and size of the fiber-optic bundles can be tailored for specific 2-D photo-sensor array sizes, and for a specific total active 1-D detector curved length and width.

It is another object of this invention to optionally make the angle between the individual fiber-optic bundles that comprise the detector face of the reorganizer adjustable, and also to make the bundles independently movable with respect to each other. This allows for quick field adjustment of the curvature of the full detector for different desired geometries, or to separate the reorganizer input faces into multiple detectors which can be placed at different user defined locations.

It is a further object of this invention to independently control the angular range and angular resolution of the detector by controlling the size of the multi-pixel array, the size of the individual pixels within that array, the grouping or "binning" of pixels within that array, the number of fiber-optic input bundles, the use of fiber-optic interfaces, the use of oblique and curved facing of the scintillation face of the fiber-optic detector, and the use of techniques to control the coherency of the scintillation process.

The present invention employs a two dimensional CCD array in lieu of multiple linear arrays. A CCD array can efficiently provide a large number of low noise photo-sensor pixels (typically 25 µm by 25 µm or less), thus providing high resolution. As the angular range of a position sensitive detector is increased, the number of pixels available to digitize the signal must increase in order to maintain the resolution. The resolution limit can be defined as the smallest angular increment that the detector system can resolve, and is limited in part, by the pixel width and the distance of the detector face (scintillation face) from the irradiated portion of the sample surface.

To create a line scan diffraction spectrum output, the individual pixels in the 2-D photo-sensor array are 'binned' into a specific array of 'composite pixels'. This is done using a computer program controlling the pixel addressing architecture. Composite pixels will act as pseudo linear photo-sensor pixels, mimicking a traditional diode array, yet providing a far greater number of pseudo linear pixels than would be feasible with actual linear diode arrays. The width of each composite pixel can be matched to the width of each incoming fiber-optic bundle, and thus will match the width of the fiber-optic detector face. The length of each composite pixel determines the resolution limit of the detector, since its length is parallel to the angular direction of the detector face. If maximum resolution is desired the composite pixel is limited to just one or two pixel lengths. At two pixel lengths a linear resolution limit of 50 µm would be achieved for a CCD utilizing a 25 µm pixel size. This is more than 2.6 times improved over the resolution limit of typical linear gas proportional detectors (130 µm). If maximum sensitivity and/or speed is required, the composite pixel length can be extended over additional pixel lengths.

The overall resolution of the diffraction pattern is affected by numerous variables including the focusing resolution of the beam entering the detector, and detector peak broadening effects. Detector components such as the scintillation coating, the fiber-optics, the fiber-optic interfaces, and the photo-sensor array will all contribute to scattering of the diffracted signal contributing to 'machine broadening' of the diffraction peaks. The resolution limit of the detector is often determined by the lowest resolution component of the detector. Thus it is advantageous to not only optimize the resolution of each component, but to generally match the resolution limits of the various components of the detector. Otherwise wasted expense and/or poorer performance might be incurred.

Optical fibers that are commonly used in flexible coherent fiber-optic bundles are typically on the order of 10 µm diameter, thus multiple optical fibers will intersect a typical photo-sensor pixel of 25 µm by 25 µm. Some optical fibers will overlap two pixels at an edge, and four pixels at a corner, thus creating some signal broadening. A certain portion of the x-rays that impinge upon the scintillation coating will be converted to visible light. This light will scatter in many directions, also leading to signal broadening. Light scattering at fiber-optic interfaces will also occur, as well as a limited amount of cross-talk between adjacent optical fibers in the fiber-optic bundles themselves. With optimized components, the resolution of fiber-optic coupled CCD x-ray area detectors have been measured at 1.5 to 2 pixel widths.

The distance of the fiber-optic scintillation faces from the irradiated spot on the sample surface also affects the resolution. For a given composite pixel length parallel to the measurement direction, moving the scintillation faces farther away from the irradiated spot will increase resolution, but decrease the angular range. Moving the scintillation faces closer to the irradiated spot will decrease the resolution, and increase the angular range. Hence, having a greater number of pixels is desirable. With a larger number of pixels available more fiber-optic bundles can be added to increase the angular range without sacrificing angular resolution.

An image intensifier can be used in the current invention if desired. It is preferred when the diffraction signals are extremely weak and/or when detector speed is far more critical than detector resolution. An image intensifier magnifies the light intensity reaching the photo-sensors thus increasing the detector sensitivity to very low light levels. The use of an image intensifier will have a limiting effect on resolution. The resolution of a micro-channel plate image intensifier is typically limited 75 µm, which is three times the size of a 25 µm pixel.

The binning of pixels in a CCD is used to mimic a very large linear diode array. However, the use of a two-dimensional CCD, combined with a fiber-optic reorganizer, has numerous advantages over using multiple linear diode arrays. A CCD array provides a much larger number of pixels (of equivalent area if they are "binned") than a single linear diode array. As described in the noted Ruud '458 patent three separate fiber-optic bundles are attached to three different linear diode arrays. In theory, this arrangement could be expanded to include, for example, ten fiber-optic bundles attached to ten separate linear diode arrays. However, using a large number of individual linear diode arrays would be very inefficient and prohibitively expensive.

Commercially available linear diode arrays cannot be readily assembled into a single compact 2-D photo-sensor array. Each such linear array operates individually as an isolated data acquisition system. For linear diode arrays to match the pixel count and total detector area available in a moderately sized 2-D CCD, numerous linear diode array acquisition systems would be required. For example, consider an 1152×1242 pixel CCD array measuring 25.9 millimeters by 27.5 millimeters (individual pixel size is 22.5 microns by 22.5 microns). To match the total detection area of the single CCD array, twenty-two linear diode arrays each measuring 2.5 millimeters by 12.8 millimeters would be required. The noted '458 Ruud patent describes three fiber-optic cables with three linear diode arrays. It would be very expensive and complex to extend that number to 22 diode arrays. A rough estimate of the cost would be four to five times greater than a CCD system, not including any of the complexities involved in electronically connecting the linear diode arrays into a single data acquisition system, or the complexity of adding image intensifiers to the system. The CCD system not only provides a single data acquisition system, but also has software control over individual pixels in the CCD array (such as ability to "bin" pixels or turn certain pixels on or off).

Using a large number of linear diode arrays geometrically arranged to form a direct x-ray sensing position sensitive detector, as in U.S. Pat. No. 4,800,580, also has numerous disadvantages. Without the use of an intervening fiber-optic reorganizer, the multiple silicon diode arrays must be fabricated, and attached both geometrically and electronically in a precise fashion, to form the 1-D position sensitive detector. It is expected that such an array would be very costly to develop, and exhibit high noise due to the large distance to be covered. In the current invention the fiber-optic reorganizer handles the burden of creating the controlled curvature 1-D detector, and leaves the photo-sensor array in its most efficient configuration. As with any silicon diode array directly exposed to typical diffraction x-ray sources, radiation damage will cause the diodes to continually degrade over time. This not only limits the life of the diode array, but necessitates that background readings be taken after every measurement, due to accumulating background noise.

Lower background noise and higher quantum efficiency can be realized in CCD arrays than in linear diode arrays. The overall background noise (dark current and read noise)

in a CCD system can be more than ten times lower than the background noise in a linear diode array when "multi-pin phasing" (a procedure provided by the CCD manufacturer to further reduce dark current) is incorporated into the CCD. The detector quantum efficiency (ratio of light input to electrical output) is approximately 10% for the linear diode array versus almost 40% for a front illuminated CCD, at a wavelength of 600 nanometers. Both the lower noise and the higher quantum efficiency make the CCD more sensitive to low incident light levels than the linear diode array. The improved light sensitivity of the CCD system can often eliminate the need to use an image intensifier.

Employing a CCD array yields compactness, making it economically feasible to incorporate an image intensifier, if desired. The multiple fiber-optic bundles of the reorganizer are rearranged into a compact 2-D configuration for mating to the CCD interface. In the example above twenty-two linear diode arrays would be spread out over roughly five times the total area, since each array is an independent device. The peripheral electronics occupy more surface area than just the active measurement area of the diode array. Thus, the active measurement area of linear diode arrays cannot be mated directly next to the active measurement area of an adjacent linear diode array. In distinction to this, all of the active area of a 2-D CCD array is contained in one continuous rectangular zone. The main advantage of compactness is the ability to use a single image intensifier for a CCD array versus numerous image intensifiers required for a large number of linear diode arrays.

The reasons discussed above provide strong justification for using a single two dimensional CCD over multiple linear diode arrays, a use novel in this technology. The present invention describes a methodology for using a two dimensional CCD in wide angle, one dimensional x-ray diffraction applications.

DETAILED DESCRIPTION OF THE INVENTION

A large angle fiber-optic detector represents a key portion of the invention. This detector is composed of three main regions, shown in FIG. 1. The first region comprises the large angle detector input ends or faces 24 upon which the x-rays impinge. The center region is a fiber-optic reorganizer 21. The third region is define by the output ends 26 of the individual fiber-optic bundles 22.

Figure 1:
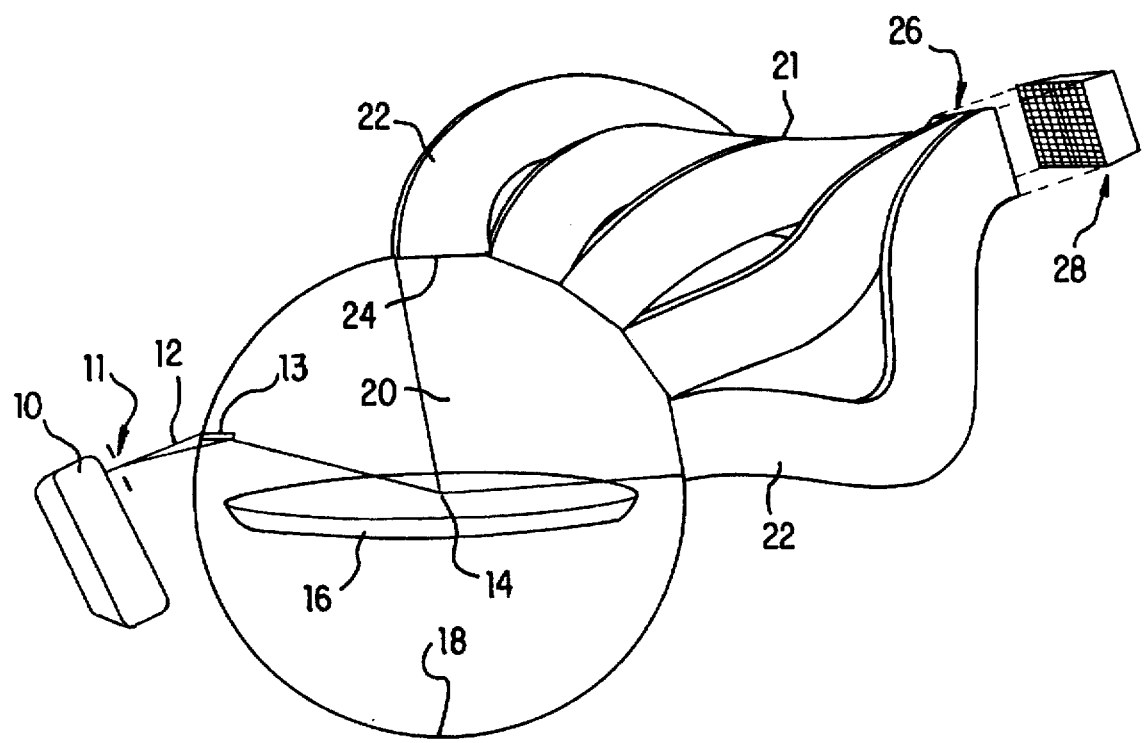
FIG. 1 is a partially schematic view of the present invention employing five fiber-optic bundles for the input bundles of an optical reorganizer, the elements located at a fixed radius from the irradiated area on the sample surface.

In FIG. 1 a conventional x-ray source 10 is shown as emitting a beam 12 of monochromatic or polychromatic x-rays through a collimator 11, and diffracted off a monochromator 13, onto a region 14 of a sample 16 of solid material. The detector circle is denoted as 18, with region 14 located at the center of this circle. The x-ray source, sample, and detector remain at fixed locations. Region 14 represents the irradiated volume of material 16 being analyzed. Diffracted and/or scattered x-rays 20 eminating from region 14 impinge upon input faces 24 of optical reorganizer 21.

An optical reorganizer 21 includes a plurality of generally rectangular optic fiber bundles or cables 22. Each of the latter has an input face 24 arranged substantially tangentially with respect to a portion of the detector circle 18, and is thus located at a nearly constant radius from region 14. Each optic fiber bundle 22 is preferably flexible in the center region and positionable to facilitate its desired angular location around the circumference of the detector circle. Conventionally, each input face 24 is coated with a scintillation coating to convert the x-radiation incident thereon to visible light. The scintillation coating is chosen based on high photon conversion efficiency, short decay times, and light output that matches that of the photo-sensor array. The thickness of the scintillation coating is chosen to balance between high x-ray stopping efficiency and minimal loss of light transmission into the fiber-optic bundles 22.

The input faces of individual bundles 22 are connected short edge-to-short edge (the short edges are mated) in a curve to coincide with the arc of the desired detector circle 18. The cross sectional length and width of bundles 22, and the number of rectangular bundles used, are chosen to match the size of the particular 2-D photo-sensor array 28 being used. Once connected short-edge to short-edge the bundles can be jacketed in a suitable rigid collar to form a fixed curved detector face.

To define detector circles of differing diameters, the individual bundles may be manually oriented, or, one can more easily make the angle between the faces of individual fiber-optic bundles 22 adjustable by attaching pivot hinges to the jacketing which can be limited to covering only the long edge of each bundle 22. The rectangular fiber-optic bundles could be further divided at the input ends to create additional pivot points in order to more closely follow the arc of the detector circle. This would be advantageous when utilizing smaller diameter detector circles and/or more than one detector circle. These pivot points can also be made detachable allowing the bundle ends to be separated from each other into subgroups. This allows adjustment of the detector faces of the subgroups at different angular regions and different radii.

The output ends of bundles 22 are denoted as 26 and are re-mated in long side-to-long side relation to form a substantially unitary rectangular array or composite. The output end of this composite face 26 is in optical alignment with the input side of a 2-D photo-sensor array 28. Photo-sensor array 28 may be a CCD (charged coupled detector) array, or other similar device.

The detector system of this invention can be utilized with all commonly used x-ray generating sources. The x-ray source for diffraction analysis can be a traditional monochromatic x-ray generator system utilizing commercially available components. Depending on the application the source might range from a few to many thousand watts and employ any of the commonly used x-ray targets, it could also make use of a polychromatic beam, synchrotron beam, or radioactive source. Since position sensitive detectors cannot readily make use of collimators (except for solar slit type) in front of the detector face, the use of a monochromator 13, placed in front of the source is highly advantageous to reduce background radition. A collimating slit 11, can also be useful in reducing background radiation.

Rather than use diverging/converging focusing beam optics, an incident beam collimator 11, and/or monochromator 13, is used, in a known manner, to create a microfocused, nearly parallel x-ray beam. The advantage of a micro-focused parallel x-ray beam is that the x-ray detector face can be fixed at different radii, with the detector face always perpendicular to the diffracted beam, and not be dependent on a particular focusing geometry. The primary disadvantages of a micro-focus parallel x-ray beam is that the irradiated volume, region 14, is very small, thus very few crystallites are illuminated for diffraction, and the x-ray flux is very low.

As noted previously, the surfaces 24 of the fiber-optic detector faces upon which the diffracted x-rays 20 impinge, are coated with of a thin scintillating film or region which converts x-rays to a lower energy electromagnetic signal, such as visible light, for subsequent transport along the fiber-optic arrays or cables 22 in a coherent manner. A film of cadmium doped zinc-sulfide powder, or gadolinium oxysulfide in a polymer binder of specific thickness, has been successfully used for this purpose. Other known scintillating materials can also be used. Techniques to maximize coherency of the scintillation process, such as partial etching of the fiber-optic bundle face 24 before coating, inclusion of scintillating fiber bundles, or collimated scintillation materials can be utilized. This would be advantageous for applications where optimal angular resolution is critical. The wavelength of light generated from the scintillating material is designed to be compatible with the optical fibers used in bundles 22, and also compatible with optimal wavelength detection range of the particular 2-D photo-sensor array 28 chosen.

The input face 24 of each fiber bundle 22 can be cut flat at a 90° angle to the fiber direction with adjacent bundle edges being connected at an offset angle to approximate the face of the detector circle, or cut with curvature to match the arc exactly. The bundles can also be cut at angles other than a 90° angle to the fiber direction. This could be desirable in cases where the incident angle of the diffracted x-rays 20 on the detector faces 24 changes over the full length of the detector.

To reorganize the fiber-optic bundles 22 from an end-to-end input configuration to a side-by-side output configuration, one starts with the desired number of flexible rectangular bundles 22 of the specific cross sectional dimensions and of appropriate length. The bundles can be connected on one side in a short edge-to-short edge configuration. They are then reinforced by applying a fixed or adjustable collar of appropriate material such as stainless steel. Optically downstream of the collar, bundles 22 are left flexible and separated so that they can be flexed into a long-edge to long-edge orientation and permanently mated with a second collar. The end that attaches to the 2-D photo-sensor array 28, is made rigid with a collar and polished flat. The detector input ends 24 are also polished, and can be completely rigid in a fixed collar, or made adjustable and detachable in a pivot collar. Leaving the center sections flexible and of sufficient length allows easy repositioning of the detector face without having to reposition any of the downstream electronics. Flexible light-tight sheathing is applied to the entire fiber-optic reorganizer such that only light generated from the diffraction process will enter the fiber-optic bundles.

The 2-D photo-sensor array 28 is required to rapidly quantify the amount of light occurring at different angular positions along the focusing circle. This can be accomplished using a CCD (charge coupled device), CID (charge induction device), or any other fiber-optic compatible 2-D multi-pixel photo-sensor array. Arrays of different sizes can be used. To cover a large angular 2θ range with high resolution, a large number of small (high resolution) pixels will be required. CCD's presently provide the greatest number of small pixels with the highest quantum efficiency and spatial resolution, and are the preferred 2-D photosensor array system for the invention, at this time. A front illuminated CCD which is coupled to a short fiber-optic interface is commercially available, and necessary for direct coupling to the fiber-optic reorganizer. Such a CCD, though not vacuum sealed, can still be cooled to $\leq -30°$ C. for efficient operation, even when mated to the multiple fiber-optic bundles.

In operation of the apparatus of FIG. 1, the diffracted beam 20 emanating from sample 16 falls on the inputs ends 24 of bundles 22. By virtue of a scintillation film on ends 24 the x-radiation is converted to light and travels along each fiber of each respective bundle 22 to its respective or homologous portion of composite output end 26. The light then falls on detector array 28 where signal therefrom are processed. It will be understood that the number of bundles 22 of reorganizer 21 may be varied, with two being the minimum number.

Figure 2:
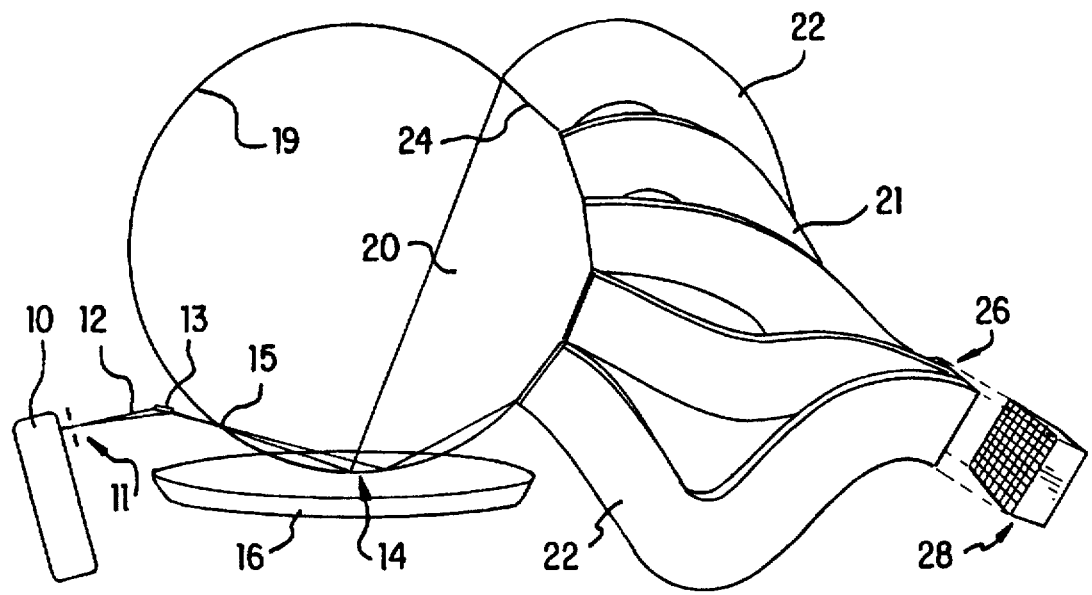
FIG. 2 is a view similar to FIG. 1, with the elements arranged in Seemann-Bohlin reflection geometry.

In FIG. 2, the apparatus and mode of operation is essentially the same as that of FIG. 1, except that it is applied to a Seemann-Bohlin (or Guinier) focusing geometry. FIG. 1 illustrates a reflection Seemann-Bohlin focusing geometry, but a transmission Seemann-Bohlin geometry can be equally accomplished. The diverging x-ray beam 12, is collimated with slit 11. An optional bent monochromator is used to monochromate, and focus the beam through a focal point 15 (in the reflection mode), onto the sample region 14. As required by the Seemann-Bohlin geometry, the irradiated volume 14, the focal point 15, and the fiber-optic bundle faces 24, are located on the circumference of a focusing circle 19. The signals from the fiber-optic reorganizer 21, and from detector 28 are similarly processed in a cotrolled manner.

In both the Seemann-Bohlin reflection and transmission geometry, the incident angle of the diffracted x-rays on the detector face will vary over the length of the detector faces 24. As shown in FIG. 2, the incident x-ray angle on the detector face decreases when going from higher to lower 2θ angles. To ensure equivalent x-ray absorption path length in the scintillation coating at all incident angles on the detector, it is important that the thickness of the scintillation coating be decreased at lower incident angles on the scintillation coating. The thickness of the scintillation coating can be controlled during its fabrication. As an approximate controlled thickness gradient, the scintillation coating can be applied at a different, but constant thickness to each fiber-optic bundle 22. The change in diffracted incidence angle will be small over the length of one fiber-optic bundle 22, compared to the change over the entire detector length, thus a uniform coating thickness on each bundle 22 will introduce negliable error.

The Seemann-Bohlin geometry utilizes diverging/converging focusing beam optics, thus requiring the detector faces 24, to all coincide with the arc of the focusing circle. The use of flat fiber-optic bundle faces 24 will create a small focusing error over the length of each fiber-optic bundle face 24. However, this error will remain small in comparison to other peak broadening effects, if the angular range of each bundle face 24 is limited to 15° or less, and preferrably 10° or less. An exact arc match can be obtained, if so desired, by grinding and polishing the faces of the fiber-optic bundles 24 to a curved shape. The primary advantages of Seemann-Bohlin focusing is that the irradiated volume, region 14, can be large, thus very many crystallites are illuminated for diffraction, and a high x-ray flux is maintained without resolution loss.

Figure 3:
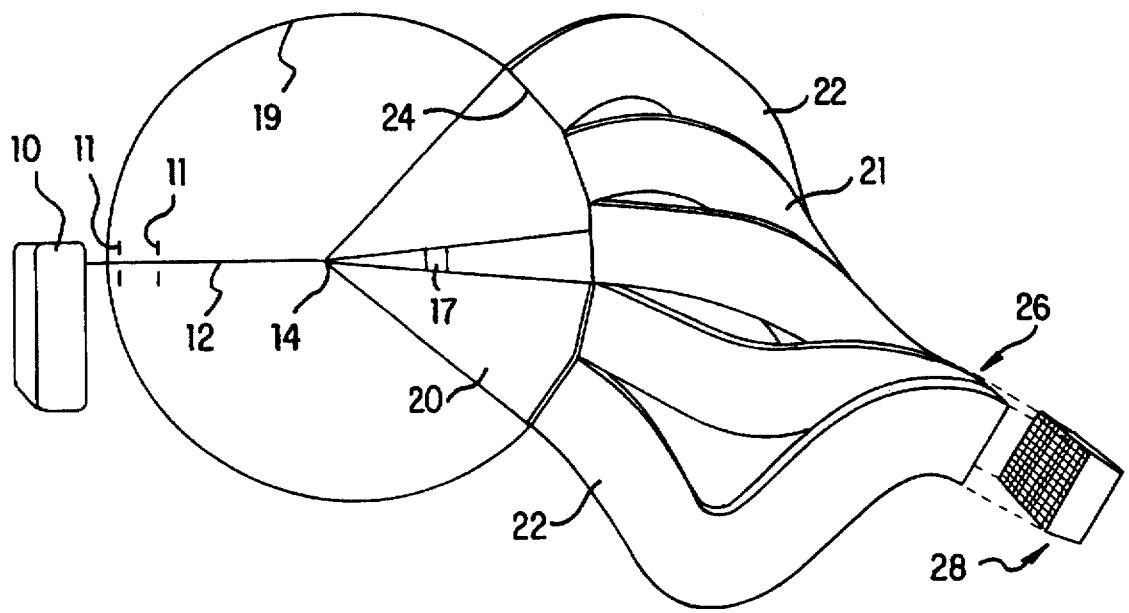
FIG. 3 is a view similar to FIG. 1, with the elements arranged in a Debye-Scherrer geometry.

In FIG. 3 the apparatus and mode of operation is similar to that of FIG. 1, except that the invention is applied to a Debye-Scherrer geometry. A very small cylindrical sample is normally prepared, and carefully positioned into location 14. A foward diffraction occurs with diffracted x-rays collected over angular ranges 20, except for a small region excluded by a conventional beam stop 17.

Figure 4:
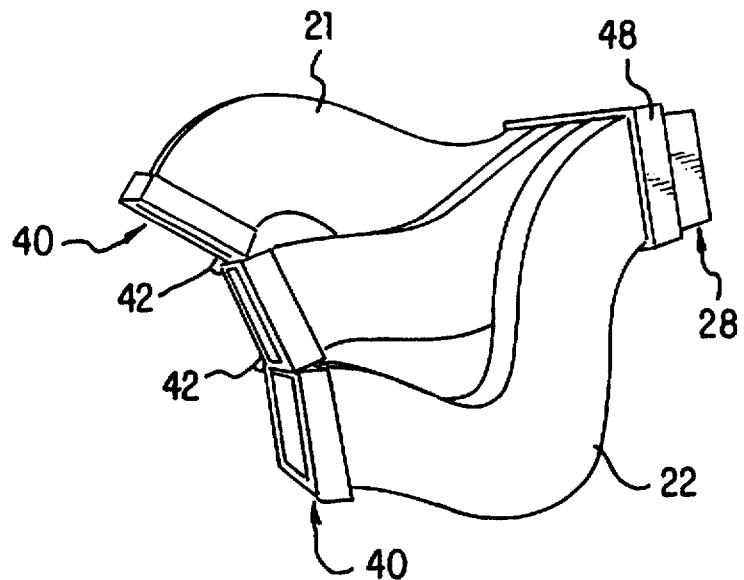
FIG. 4 is a view similar to FIGS. 1 and 2 showing hinged rigid collars on the input ends of the input optic fiber bundles and a single collar on the output end of the optic reorganizer.

In FIG. 4, optical reorganizer 21 is illustrated as having three bundles 22, with the input end of each bundle having there around a collar 40, such as one of stainless steel, or other suitable rigid material. Each collar 40 is rectangular, matching the shape of its respective bundle and bundle end. The collars provide mechanical protection to the ends of the fiber-optic bundles 24. Optionally, the narrow ends of adjacent collars 40 are coupled by hinges 42 to permit adjustment of the input faces 24 for various diameter focusing circles 19 (FIG. 2), or detector circles 18 (FIG. 1). Similarly, a rigid collar 48 may be attached to the output end 26 of the optical reorganizer for mechanical protection, and a method of attaching the reorganizer to the 2-D photo-sensor array. It is understood that collars 40 and 48 are optional, but make the optic reorganizer easier to reposition, and more robust.

Figure 5:
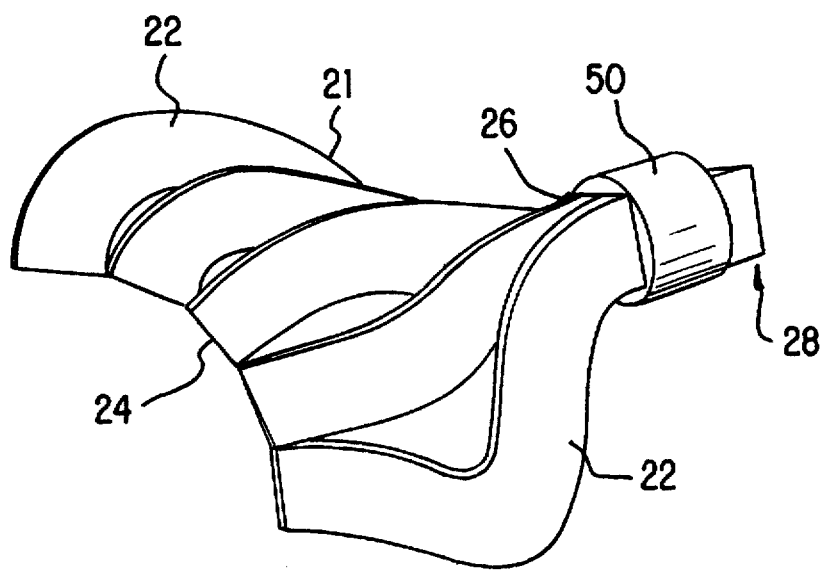
FIG. 5 is a partially schematic view showing an optic coupling between the output end of the optical reorganizer and the multipixel photodetector.

FIG. 5 illustrates the use of a fiber-optic interface 50 located between output end 26 of the reorganizer and the input face of multipixel photodetector 28. The interface is composed of a bundle of parallel optic fibers, similar to those defining each bundle 22 of the reorganizer. The fiber-optic interface is applied directly to the CCD face by the CCD manufacturer, as an option, since direct fiber-optic coupling to the CCD array is extremely difficult for those not experienced with the procedure. The fiber-optic interface allows the CCD user to easily mate a fiber-optic bundle to the CCD by direct pressure contact using indexed matched optical gel.

The fiber-optic interface 50, also enables the incorporation of a commercially available fiber-optic compatible micro-channel plate image intensifier. The image intensifier is useful in applications where very low x-ray flux predominates. Though not shown in FIG. 5, the image intensifier can be placed between the fiber-optic output end 26 and the fiber-optic interface 50.

To create a one-dimensional diffraction spectrum output, the active pixels 52 are grouped or "binned" into a continuous series of composite pixels 55 (see FIG. 6) using software supplied by a manufacturer of CCD controllers. An example of such software is WinView or WinSpec (trade names) marketed by Princeton Instruments Inc. of Trenton, N.J. The WinView and WinSpec software provides a generic method for binning both operative pixels 52 and inoperative (non-reading) pixels 54.

Figure 6:
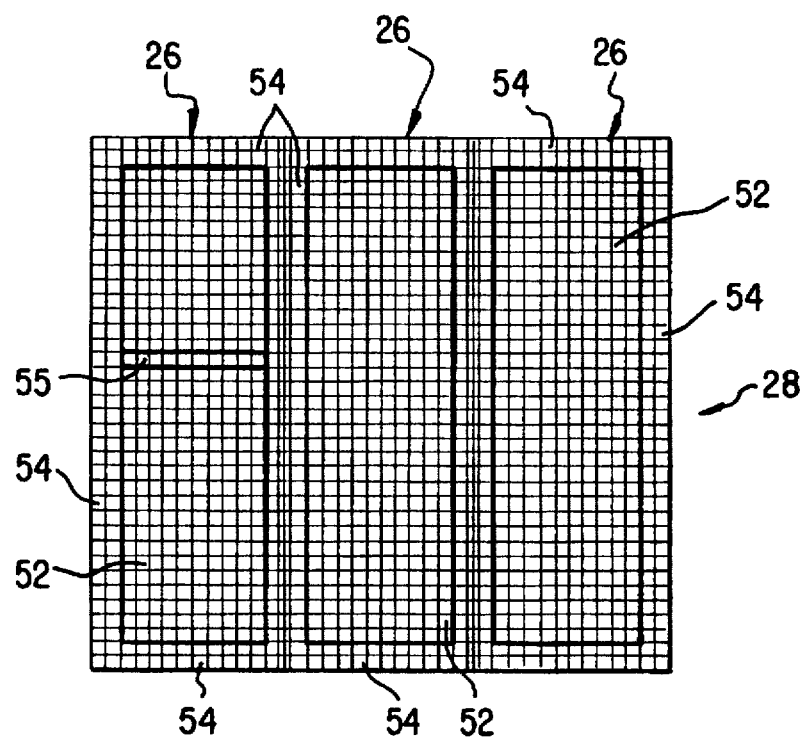
FIG. 6 is a plan view of the input face of the multipixel photodetector which illustrates the technique of "binning".

In order to achieve the appropriate grouping of both inoperative and operative pixels, the binning procedure illustrated in FIG. 6 is followed, and is now described. This procedure will accomplish three things. First, it will create a digitized 1-D or line scan output. Second, it will minimize interference (cross-talk) between adjacent fiber optic bundles at the 2-D photo-sensor array interface 26/28, and third, it will compensate for minor misalignment between the fiber-optics and the photo-sensor array.

According to the first aspect of the binning procedure, a particular "binning" of pixels is necessary to make the 2-D CCD array function as a pseudo linear photo-sensor array. The three vertically disposed rectangular elements 26 illustrated in FIG. 6 represent the projection of a three bundle reorganizer onto the input face of detector 28 whose active individual pixels are each denoted as 52. In commercial CCD's the actual number of pixels is much greater than the number shown in detector 28. Those active pixels 52 are bordered by inactive pixels 54 which occur in the vicinity of the perimeter of each output end of the fiber-optic bundles 22. Inactive pixels 54 are rendered inactive in the sense that the signals generated by light striking them are effectively not processed. The signals generated by the active interior pixels 52 are processed.

For each rectangular fiber-optic bundle 22 output end a continuous repeating series of composite pixels 55 form the equivalent of a linear photo-sensor array. The last composite pixel 55 located at both ends of each fiber-optic output array is linked using software to the last composite pixel 55 of the adjacent fiber-optic output bundle end to create a continuous string of composite pixels 55 extending over all of the fiber-optic bundles 22. This continuous string of composite pixels 55 will effectively measure along the continuous string of input fiber-optic faces 24, the latter comprising the detector face. The output from the 2-D photo-sensor array 28 will thus recreate the continuous one-dimensional diffraction spectrum that was detected over all of the fiber-optic bundle input ends 24. The output is digitized, and can be stored or displayed on a computer in a manner similar to x-ray diffraction spectrums obtained by modern conventional scanning diffractometers.

To obtain maximum resolution the composite pixel 55 is limited one pixel length in the direction parallel to detector circle 18, or focusing circle 19, and the maximum number of pixels wide perpendicular to either circle (as depicted in FIG. 6). The maximum width of composite pixel 55 is determined by the narrowest dimension of the output end of each fiber-optic bundle 22, minus the number of inoperative pixel 54 columns within the border of each fiber-optic bundle 22. Discounting scattering effects due to other factors, the resolution limit would be the length of one pixel. Binning pixels together perpendicular to the detector or focusing circle improves the photo-sensor sensitivity and speed, without affecting the resolution. In cases where detector sensitivity is much more critical than detector resolution the composite pixels 55 can be increased to more than one pixel length in the direction parallel to detector circle 18, or focusing circle 19. For example a composite pixel that is two pixels long and the maximum number of pixels wide, will have twice the measuring area but half the resolution as the composite pixel that is only one pixel long. In most cases it will be desirable to match the composite pixel resolution limit to the other resolution limiting factors such as beam focus, scintillation coating resolution limit, and image intensifier resolution limit.

According to the second aspect of the binning procedure, rendering inoperative those pixels located in the near vicinity of the border between each fiber-optic bundle 22 output end will eliminate possible light interference between adjacent bundles 22. High light intensity occurring at diffraction peak locations could spill over to an adjacent fiber-optic bundle giving a false signal. This occurs by cross talk occurring in adjacent optical fibers, but is usually limited to no more than four fiber widths, or about 40 microns. In FIG.

6 three vertical pixel columns in the vicinity of the interface are made inoperative. Based on a typical pixel size of 25 microns by 25 microns the total inoperative width of 75 microns would ensure no interference between adjacent fiber-optic bundles 22, with only a small sacrifice in usable CCD area.

According to the third aspect of the binning procedure a similar set of pixels located near the external borders of the output face 26 are rendered inoperative pixels to allow for minor translational and angular misalignment between the photo-sensor array 28 and fiber-optic output end 26. It is important to minimize the number of pixels rows made inoperative in the vicinity of the short edges each fiber-optic bundle 22. This will minimize the angular gap between sequential fiber-optic bundles 22.

The second and third aspect of the binning procedure can also be accomplished by incorporating a non light transmitting layer of appropriate thickness between each long edge-to-long edge fusion region and around the perimeter of the output end 26, and reducing the length and width of each bundle accordingly, such that the total fiber-optic bundle assembly still fits within the multi-pixel array boundaries.

As an added improvement over traditional scanning diffractometers that cannot readily discriminate signal strength perpendicular to the scan direction, one can scan across isolated composite pixels 55 to obtain microstructure information. A logical procedure for doing this would be to first obtain a traditional one-dimensional diffraction spectrum. Once diffraction peak locations have been identified the operator can go back and scan a limited number of composite pixels in the peak locations, perpendicular to the focusing circle. This perpendicular scan will be limited to the width of the fiber-optic bundle, minus pixels that have been made inactive, and essentially observes a small segment of the diffraction Debye ring. This procedure can yield information on the average grain size and orientation.

The operating software of a CCD system allows one to group or "bin" pixels as desired. By combining numerous pixels (perpendicular to the focusing arc) into one composite pixel improved counting statistics are achieved since there is more detector area devoted to each angular increment. For a given size CCD array, choosing the number of fiber-optic bundles to use depends upon the desired angular range, resolution, focal distance, and signal collection area of each angular pixel of the diffraction geometry. A larger number of bundles will allow a greater angular range at equivalent resolution, assuming no change in the detector-to-sample distance and no fiber-optic tapers are area for each result in smaller signal collection area for each composite pixel. The maximum angular resolution is achieved by limiting composite pixel length to one pixel parallel to the detector or focusing arc, while signal strength is maximized by combining as many pixels as possible perpendicular to the arc.

A typical pixel size in many front illuminated CCD's is 22.5 μm by 22.5 μm. Based on that size the angular resolution limit would be 0.025° for a 2 inch (5.08 cm) detector-to-sample distance, and 0.0165° for a 3 inch (7.62 cm) distance using non-tapered fiber-optics. Other components in the system such as the scintillation coating, fiber-optics, and optional image intensifier, as well as beam geometry, will likely limit the actual resolution to values greater than the limit set by the pixel size. Thus it is likely that the composite pixel length will be set to a preferred range of 2 to 10 pixels, based on a 22.5 μm by 22.5 μm pixel size.

Figure 7:
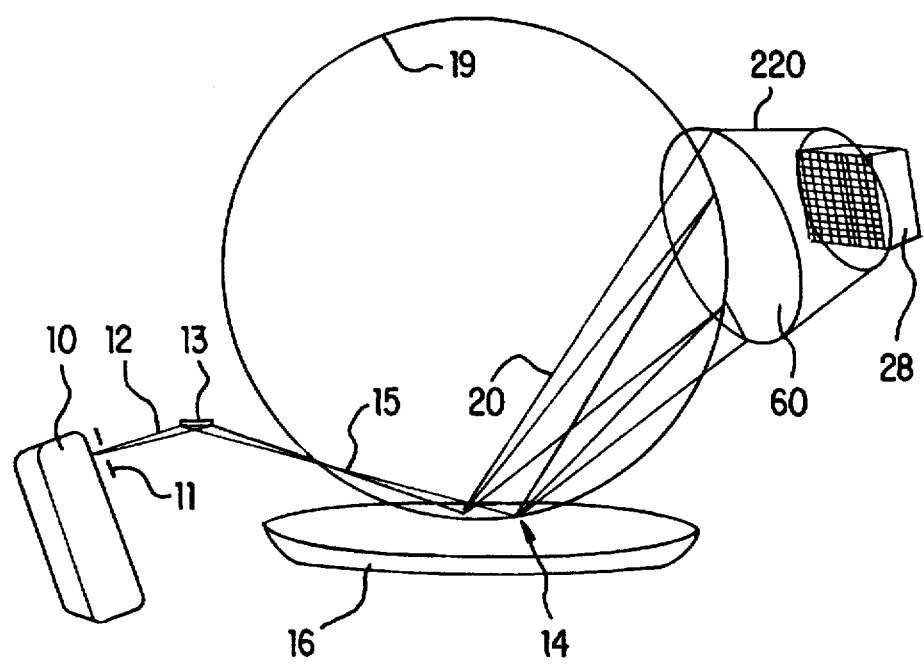
FIG. 7 is a partially schematic view illustrating the relation between this invention and a prior art construction.

FIG. 7 illustrates the relation of this invention to a prior art construction, that is shown in U.S. Pat. No. 4,489,425 issued to Borgonovi. The detector illustrated in FIG. 7 is also similar CCD based area x-ray detectors produced by Nonius Delft Instruments (Delft, Netherlands), Molecular Structure Corporation (The Woodlands, Texas), and Siemens Analytical (Madison Wis.). In the Borgonovi patent, a generally 2-D tapered fiber-optic bundle 22 (denoted as 220 and shown in phantom lines in FIG. 7) has a circular, flat scintillating input face 21 (denoted as region 60 in FIG. 7), which is optically coupled on the smaller tapered side to a photodetector 25, the latter corresponding to multipixel detector 28 of this invention. In Borgonovi, a cone of diffracted x-rays falls on the input scintillating face 21 of fiber-optic bundle 22. The face is a flat two dimensional surface which is coated with a scintillation layer. The x-rays are converted to visible light which is transported to the tapered flat two dimensional output face of fiber bundle 22. The light impinges upon photodetector 25, which is also has flat two dimensional face.

The Borgonovi and related area x-ray detector systems are designed and optimized for x-ray detection over a limited two dimensional area. Given the same size photo-sensor array and identical beam geometry (as shown in FIG. 1 and FIG. 2), the angular range of the fiber-optic reorganizer 21 of this invention is significantly larger over a single detector circle or focusing circle than the 2-D detector, even when considering a 2:1 taper ratio. The single 2-D to 2-D fiber optic taper 220 does not enable groups of pixels in the CCD array to be separated to detect widely separated angular regions along a single detector circle or focusing circle. The fiber-optic 2-D to 1-D reorganizer 21 is the critical component which enables full use of the CCD pixels on a single detector circle or focusing circle.

Unlike the Borgonovi and related area x-ray detectors the current invention can also be readily applied to focusing x-ray geometries (as illustrated in FIG. 2). The micro-focus, near parallel beam geometry of FIG. 1 does not require that each fiber-optic bundle flat face cover less than 15° 2θ, while the Seemann-Bohlin focusing beam geometry in FIG. 2 does. FIG. 7 shows that when the flat 2-D area detector is applied to focusing Seemann-Bohlin geometry there are only two zones of the input surface of 220 which intersect the focusing arc, and therefor receive focused diffracted x-rays 20. These are shown as dotted lines within diffracted x-ray region 20 converging to focal points at the detector face. Since the entire detector face is comprised of one flat surface, it cannot coincide with the focusing arc over a large angular range ($\geq 15°$ 2θ) without incurring a significant defocusing error. The 2-D tapered fiber-optic array is a single rigid unit. To cover an angular range much larger than 15° 2θ would require that the face be ground and polished with an inside curve to match the focusing circle. This adds significant cost to the fiber-optic and limits its use to only one size focusing circle, and still does not enable the area detector to match the angular range of the current invention.

The fiber-optic reorganizer of the present invention however, is made of multiple rectangular cross-section fiber-optic arrays (five bundles are shown in FIGS. 1 and 2). The detector faces 24 (where the x-rays impinge) of these arrays can be polished flat, and the bundles subsequently connected at an offset angle to nearly coincide with the curve of the focusing circle. Although each face 24 will not exactly match the curvature in the focusing circle, each face covers only a small angular portion of the focusing circle ($\leq 15°$), thus the degree of arc mismatch, and therefor the amount of defocusing, is very small compared to the single 2-D detector that has a flat detector surface, as set out in the description of FIG. 7.

In contrast to the Borgonovi area detector, the multiple rectangular fiber-optic bundles of the 1-D to 2-D reorganizer 21 of the present invention can be easily repositioned for different size detector circles 18 and focusing circles 19 by changing the offset angle between the bundles 22 at the detector faces 24. The bundles can also be split up into different zones on the focusing circle. This is desirable in cases where diffraction peaks of interest occur over a very large angular range. They can also be placed at different distances to the irradiated spot on the sample surface (on different diameter circles) if so desired. A single 2-D fiber-optic bundle, such as 22 of Borgonovi, whether curved or not, cannot be readily adjusted to different focusing geometries simply because it is one rigid unit. It can be placed at different angular positions on focusing circle or detector circle, but it will not function on a different size circles.

As a first example, four rectangular bundles, each with a cross sectional dimension of 27.4 mm by 1.7 mm can be attached end-to-end on a 3 inch (76.2 mm) radius detector circle, employing the beam geometry described in FIG. 1, to provide an angular range of about 91°. The width of the input faces 24 are finite, yet all of the faces essentially define a 1-D arc. The angular range of each fiber-optic bundle would be about 22.7° 2θ. The four fiber-optic bundles could be used to intersect a CCD array of 256 pixels by 1024 pixels (each pixel measuring 27 µm by 27 µm for a total array size of 6.9 mm by 27.6 mm). The four bundles are reorganized from a short edge-to-short edge configuration at the scintillation face to a long edge-to-long edge configuration at the CCD array face. The width of each fiber-optic bundle covers 64 pixels, or 1.73 min. A composite pixel is created by combining a single row of 60 pixels across the width of each fiber-optic array. Two pixel columns at each long edge are deactivated to eliminate cross talk between adjacent fiber-optic bundles, and compensate for positioning uncertainty. The bundle length (27.5 mm) is just slightly less than CCD array length (27.6 mm) such that two pixel rows at the short ends of the output fiber-optic bundles are not used. This allows for slight positioning uncertainty in the fiber-optic bundle long dimension. Thus each rectangular fiber-optic array can intersect a linear composite pixel array 1020 pixels long and one composite pixel (made up of 60 individual pixels) wide. Four fiber-optic bundles would result in 4 times 1020, or 4080 total composite pixels. The resolution limit would be 0.022° 2θ. Increasing the composite pixel size to 2 pixels by 60 pixels, would reduce the number of composite pixels to 510 per output bundle, or a total of 2040 pixels for all four bundles. The resolution limit would drop to 0.045° 2θ.

In another example a front illuminated fiber-optic coupled CCD chip with 770×1152 pixels (each pixel measuring 22.5 µm on a side for a total array size of 17.3 mm by 25.9 mm) could be used to mate with 8 fiber-optic bundles each with a cross section of 2.16 mm by 25.7 mm. If applied to a Seemann-Bohlin reflection geometry (FIG. 2) utilizing a 3.5 inch (89 mm) radius focusing circle the total angular range would be ~66.4° 2θ using and incident angle of 10° and diffracted angular limits of 14° and 80.4° respectively. In this case the width of the fiber-optic bundle would cover 96 pixels with 92 made operative. The maximum number of composite pixels would be 9152 (=8×1144), figuring a one pixel length of the composite pixel, and 4 pixel lengths at each bundle short edge location that are made inoperative. The angular resolution limit would be 0.007° 2θ. Using a composite pixel size of 4 pixels by 92 pixels would reduce the total number of composite pixels to 2288, providing four times the composite pixel size, yet still provide an angular resolution of 0.029° 2θ (66.4÷2288=0.029).

In the Seemann-Bohlin focusing geometry, defocusing errors of each flat fiber-optic bundle face, and variable x-ray incidence on the detector face, must both be considered. The angular range of each bundle will be 8.3°, thus defocusing due the flat bundle faces will be minimal, well below the desired limit of 15° per bundle. To compensate for change in angle of incidence of x-rays impinging on the detector surface, the thickness of the scintillation layer is reduced as the angle of incidence on the detector surface is reduced. At near perpendicular angles a Gd2O2S:Tb film with a density of ~11 miligrams/cm², corresponding to a film thickness of ~50 µm, works well as a scintillation coating for copper radiation. To match the equivalent incident path length at 90°, the thickness is reduced to 43 µm at a 60° incident angle. At a 30° incident angle the thickness is reduced to 25 µm, and at a 15° incident angle the thickness is reduced to 13 µm. The film thickness can be controlled as part of dispersion settling process for making the film. A uniform thickness set for the angular midpoint of each bundle can be applied in separate coating operations, or a thickness gradient coating could be applied simultaneously to bundle faces appropriately positioned in the settling process. The maximum path length of 50 µm limits the 'smearing' effect to just two pixel lengths at very low incidence angle, and is well within the example composite pixel measuring 4 by 92 individual pixels.

In the above example, a 2:1 fiber-optic taper would increase the angular range at 3.5 inches to 132.8° 2θ, while the resolution limit for one composite pixel length would be changed to 0.014°. The taper could be applied at either of two locations. It could be applied to the ends of each of the flexible fiber-optic bundles prior to mating them to form the curved detector face. This would require a separate taper for each fiber-optic bundle. It could also be applied as a single tapered slug mated directly to the CCD chip, and combined with fiber-optic bundles having a larger rectangular cross section. The latter option offers the simplicity of only one required taper and would be generally favored over the prior option.

When a taper is applied to a 2-D fiber-optic array each of the individual optical fibers are drawn down from a larger diameter to a smaller diameter. On the large end the optical fibers might be 20 microns in diameter and on the small end the fibers might be 10 microns in diameter. Light is transported through each optical fiber separately (there is some light interference between adjacent fibers but it is generally limited to 2 fiber widths) as it tapers. A 2-D tapered array preserves the detail of an image, while either reducing or increasing its size. A 2:1 taper might be a 2 inch diameter bundle that is drawn down to 1 inch diameter, made by heating the bundle to the softening point of glass and drawing it down to the desired diameter. Rectangular fiber-optic tapers are commercially available from Schott Fiber-Optics, Southbridge, Mass.

We claim:

1. An apparatus for the measurement of properties of a solid material by analysis of x-rays diffracted and/or scattered from the material, the apparatus including an x-ray source for directing a beam of x-rays onto the solid material, a plurality of separate fiber-optic cables having respective input and output ends, said input ends coated with a scintillation material for converting x-radiation into light radiation, said input ends arranged along an arc and being substantially coplanar and being divisible into two or more subgroups, said input ends comprising each subgroup, said input ends being contiguous to thereby define a substantially continuous input arc along any subgroup and hence defining a substantially one dimensional array, said cable output ends arranged side by side to form a two dimensional array, a two dimensional photodetector array in optical alignment with said two dimensional cable output ends, whereby some of the x-rays diffracted and/or scattered from the solid material upon impingement by the x-ray source strike the input ends of the fiber-optic cables and are converted by the scintillation material to light radiation, the light radiation exiting from the output ends of the cable array and thence to the photodetector array.

2. The apparatus of claim 1 wherein said cables are of uniform rectangular transverse cross section and have a longer and a shorter dimension.

3. The apparatus of claim 1 wherein said cable input ends are arranged so that each is substantially tangent to a portion of the circumference of a circle.

4. The apparatus of claim 1 wherein said cable input ends are provided with surrounding collars, adjacent of said collars being hinged together at variable offset angles and able to be disconnected.

5. The apparatus of claim 1 including a optic fiber interface located between said photodetector array and said output ends of said cables.

6. The apparatus of claim 1 wherein said scintillation coating on each of said input ends is of a variable thickness.

7. The apparatus of claim 1 wherein said apparatus is configured in either a parafocusing Bragg-Brentano, parallel beam geometry, Seemann-Bohlin geometry, Guinier geometry, or Debye-Scherrer geometry.

8. A method for analyzing properties of a solid material, the method including the steps of directing a beam of x-rays onto the solid material, detecting the resultant diffracted and/or scattered x-radiation from the material at spaced regions along an arc, said spaced regions each substantially lying in a plane and being divisible into two or more subgroups, said regions in any subgroup being contiguous to thereby define a substantially continuous input arc along any subgroup, converting said x-radiation to light radiation, conveying said light radiation to individual pixels of a two dimensional photo-detector array, binning said pixels of said photo-detector array into composite pixels to form a one-dimensional spectral output for analysis, storage, and/or display, converting said x-radiation to light radiation, conveying said light radiation to individual pixels of a two dimensional photo-detector array, binning said pixels of said photo-detector array into composite pixels to form a one-dimensional spectral output for analysis, storage, and/or display.

9. The method of claim 8 wherein said light is conveyed by cables composed of individual optic fibers.

10. A method for analyzing properties of a solid material, the method including the steps of directing a beam of x-rays onto the solid material, detecting the resultant diffracted and/or scattered x-radiation from the material at spaced regions along an arc, said spaced regions each substantially lying in a plane and being divisible into two or more subgroups, said regions in any subgroup being contiguous to thereby define a substantially continuous input arc along any subgroup, converting said x-radiation to light radiation which enters respective input ends of fiber-optic bundles, each said bundle having an output end, each said bundle having a cross-sectional length greater than its cross-sectional width, conveying said light radiation along said fiber-optic bundles from said input ends to said output ends to individual pixels of a two dimensional photo-detector array, binning said array, binning said pixels of said two dimensional photodetector array into composite pixels to recreate a one-dimensional spectral diffraction spectrum which is detected at said fiber-optic input ends, said binning step including forming a continuous repeating series of linear composite pixels, each said composite pixel having a length greater than its width, and whose long dimension is less than said cross-sectional width of each fiber-optic output end, whereby said composite pixels are continuously connected by their long edges to form an equivalent linear array whose length is less than said cross-sectional length of each fiber-optic output end, and whereby the last composite pixel at the end of each said fiber-optic output end is linked to the last composite pixel of an adjacent fiber-optic bundle end to create a continuous string of one-dimensional composite pixels.

* * * * *